(12) United States Patent
Tegels

(10) Patent No.: US 9,839,415 B2
(45) Date of Patent: Dec. 12, 2017

(54) APEX CLOSURE DEVICE

(71) Applicant: St. Jude Medical, LLC, Abbott Park, IL (US)

(72) Inventor: Zachary J. Tegels, Minneapolis, MN (US)

(73) Assignee: St. Jude Medical, LLC, Abbott Park, IL (US)

(*) Notice: Subject to any disclaimer, the term of this patent is extended or adjusted under 35 U.S.C. 154(b) by 4 days.

(21) Appl. No.: 13/794,105

(22) Filed: Mar. 11, 2013

(65) Prior Publication Data

US 2013/0253577 A1   Sep. 26, 2013

Related U.S. Application Data

(63) Continuation-in-part of application No. 13/146,789, filed as application No. PCT/US2010/000249 on Jan. 29, 2010.

(60) Provisional application No. 61/206,441, filed on Jan. 30, 2009.

(51) Int. Cl.
    *A61B 17/00* (2006.01)
    *A61B 17/064* (2006.01)
    *A61B 17/34* (2006.01)
    *A61B 17/04* (2006.01)

(52) U.S. Cl.
    CPC ...... *A61B 17/0057* (2013.01); *A61B 17/0644* (2013.01); *A61B 17/34* (2013.01); *A61B 17/00491* (2013.01); *A61B 17/0469* (2013.01); *A61B 2017/00243* (2013.01); *A61B 2017/00247* (2013.01); *A61B 2017/00623* (2013.01); *A61B 2017/00867* (2013.01); *A61B 2017/3425* (2013.01); *A61B 2017/3454* (2013.01)

(58) Field of Classification Search
    CPC .............. A61B 17/0057; A61B 2017/00659
    USPC ................ 606/213, 214, 215, 232
    See application file for complete search history.

(56) References Cited

U.S. PATENT DOCUMENTS

| 4,291,690 A |   | 9/1981 | Jessen |
|---|---|---|---|
| 4,900,303 A | * | 2/1990 | Lemelson ............. 604/514 |
| 5,330,437 A |   | 7/1994 | Durman |

(Continued)

FOREIGN PATENT DOCUMENTS

| EP | 1671596 A1 | 6/2006 |
|---|---|---|
| WO | 9631165 A1 | 10/1996 |

(Continued)

OTHER PUBLICATIONS

International Search Report and Written Opinion, PCT/US2010/00249, dated Jun. 1, 2010.

(Continued)

*Primary Examiner* — Tuan V Nguyen
*Assistant Examiner* — Chima Igboko
(74) *Attorney, Agent, or Firm* — Lerner, David, Littenberg, Krumholz & Mentlik, LLP

(57) ABSTRACT

Wound closure devices, systems, and methods may be used to close an opening, such as a puncture wound or incision, formed in tissue, such as heart tissue. A wound closure device may be configured and adapted to be placed within the puncture wound or incision to close and/or seal the puncture wound or incision. A bioadhesive may be used to strengthen the closure and/or seal of the puncture wound after placement of the wound closure device relative to the puncture wound.

13 Claims, 13 Drawing Sheets

(56) References Cited

U.S. PATENT DOCUMENTS

| | | | |
|---|---|---|---|
| 5,395,342 A | 3/1995 | Yoon | |
| 5,603,702 A | 2/1997 | Smith et al. | |
| 5,649,959 A * | 7/1997 | Hannam et al. | 606/213 |
| 5,653,730 A * | 8/1997 | Hammerslag | 606/214 |
| 5,810,884 A * | 9/1998 | Kim | 606/213 |
| 5,882,340 A | 3/1999 | Yoon | |
| 6,113,641 A * | 9/2000 | Leroy | A61B 17/0057 600/37 |
| 6,174,322 B1 * | 1/2001 | Schneidt | 606/213 |
| 6,475,177 B1 * | 11/2002 | Suzuki | A61B 17/0057 604/11 |
| 7,008,439 B1 * | 3/2006 | Janzen et al. | 606/213 |
| 7,771,454 B2 * | 8/2010 | Michlitsch | 606/213 |
| 7,862,500 B2 * | 1/2011 | Khairkhahan et al. | 600/16 |
| 8,182,530 B2 | 5/2012 | Huber | |
| 8,257,389 B2 * | 9/2012 | Chanduszko et al. | 606/213 |
| 8,454,708 B2 * | 6/2013 | Kutsko et al. | 623/23.65 |
| 8,529,430 B2 * | 9/2013 | Nikolic et al. | 600/37 |
| 8,870,914 B2 | 10/2014 | Hoffman et al. | 606/213 |
| 2002/0072767 A1 * | 6/2002 | Zhu | 606/213 |
| 2002/0165581 A1 * | 11/2002 | Brucker | 606/213 |
| 2002/0183787 A1 * | 12/2002 | Wahr et al. | 606/213 |
| 2005/0004158 A1 * | 1/2005 | Iyer et al. | 514/291 |
| 2005/0043759 A1 * | 2/2005 | Chanduszko | A61B 17/0057 606/213 |
| 2006/0074484 A1 | 4/2006 | Huber | |
| 2006/0167468 A1 | 7/2006 | Gabbay | |
| 2007/0032823 A1 * | 2/2007 | Tegg | 606/232 |
| 2007/0083229 A1 * | 4/2007 | Deutsch | 606/213 |
| 2007/0123816 A1 * | 5/2007 | Zhu et al. | 604/57 |
| 2007/0186934 A1 | 8/2007 | DeLuca | |
| 2007/0198060 A1 * | 8/2007 | Devellian et al. | 606/213 |
| 2008/0004657 A1 * | 1/2008 | Obermiller et al. | 606/213 |
| 2008/0114395 A1 * | 5/2008 | Mathisen | A61B 17/0057 606/215 |
| 2008/0215087 A1 * | 9/2008 | Pavcnik et al. | 606/213 |
| 2008/0255650 A1 * | 10/2008 | Kelley | A61F 2/064 623/1.2 |
| 2008/0312684 A1 * | 12/2008 | Drasler et al. | 606/213 |
| 2009/0062844 A1 * | 3/2009 | Tekulve et al. | 606/213 |
| 2009/0069843 A1 * | 3/2009 | Agnew | 606/213 |
| 2009/0088793 A1 * | 4/2009 | Bagaoisan et al. | 606/213 |
| 2009/0171388 A1 * | 7/2009 | Dave et al. | 606/213 |
| 2009/0177225 A1 * | 7/2009 | Nunez | A61B 5/1427 606/213 |
| 2009/0216265 A1 * | 8/2009 | DeVries et al. | 606/213 |
| 2009/0216267 A1 * | 8/2009 | Willard et al. | 606/213 |
| 2009/0227938 A1 * | 9/2009 | Fasching et al. | 604/57 |
| 2009/0254110 A1 * | 10/2009 | Bagaoisan et al. | 606/185 |
| 2013/0006297 A1 * | 1/2013 | Drasler | 606/213 |

FOREIGN PATENT DOCUMENTS

| | | |
|---|---|---|
| WO | 97/17026 A1 | 5/1997 |
| WO | 9953852 | 10/1999 |
| WO | 03049619 A2 | 6/2003 |

OTHER PUBLICATIONS

Extended European Search Report for Application No. 17155634.3 dated May 17, 2017.

\* cited by examiner

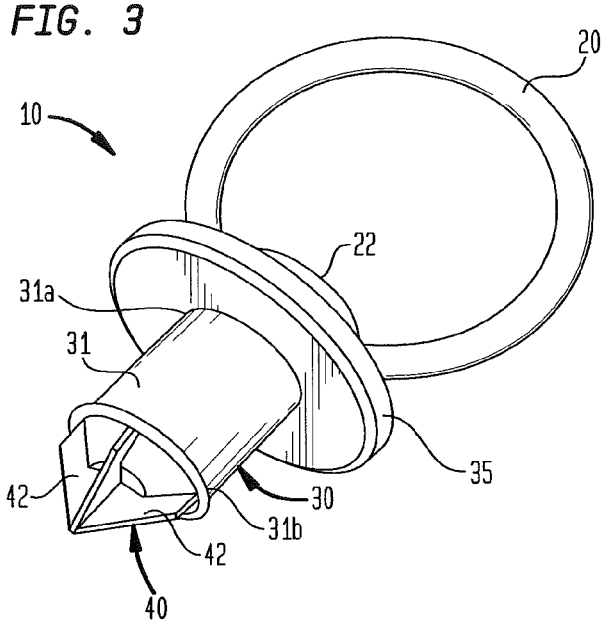
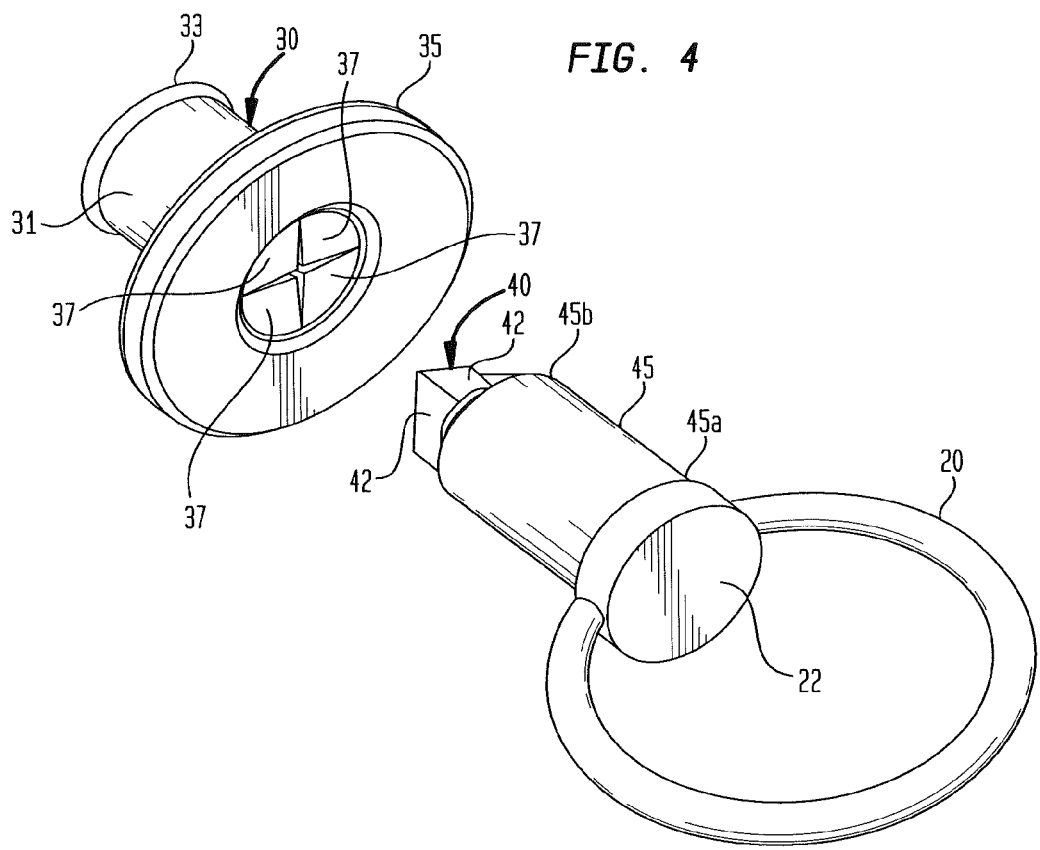

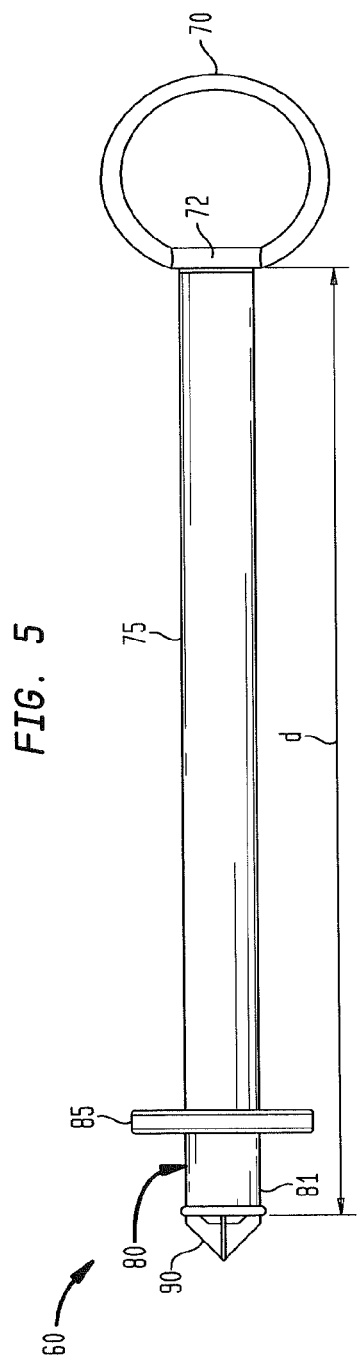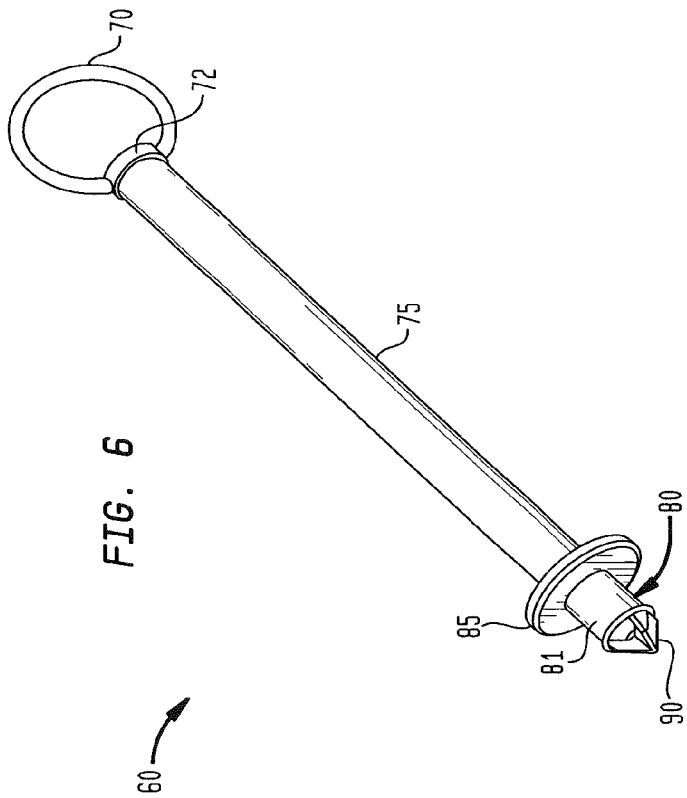

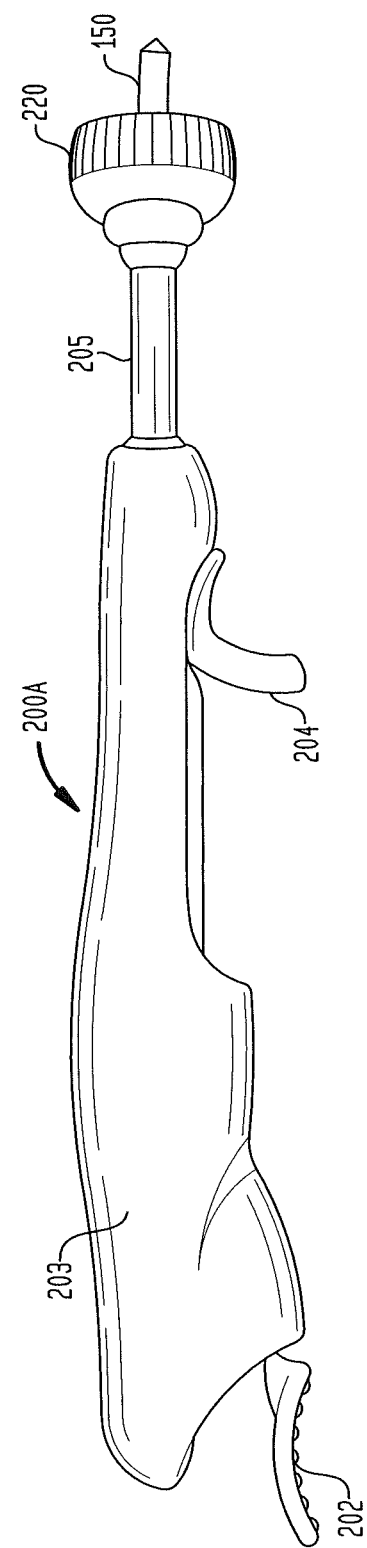

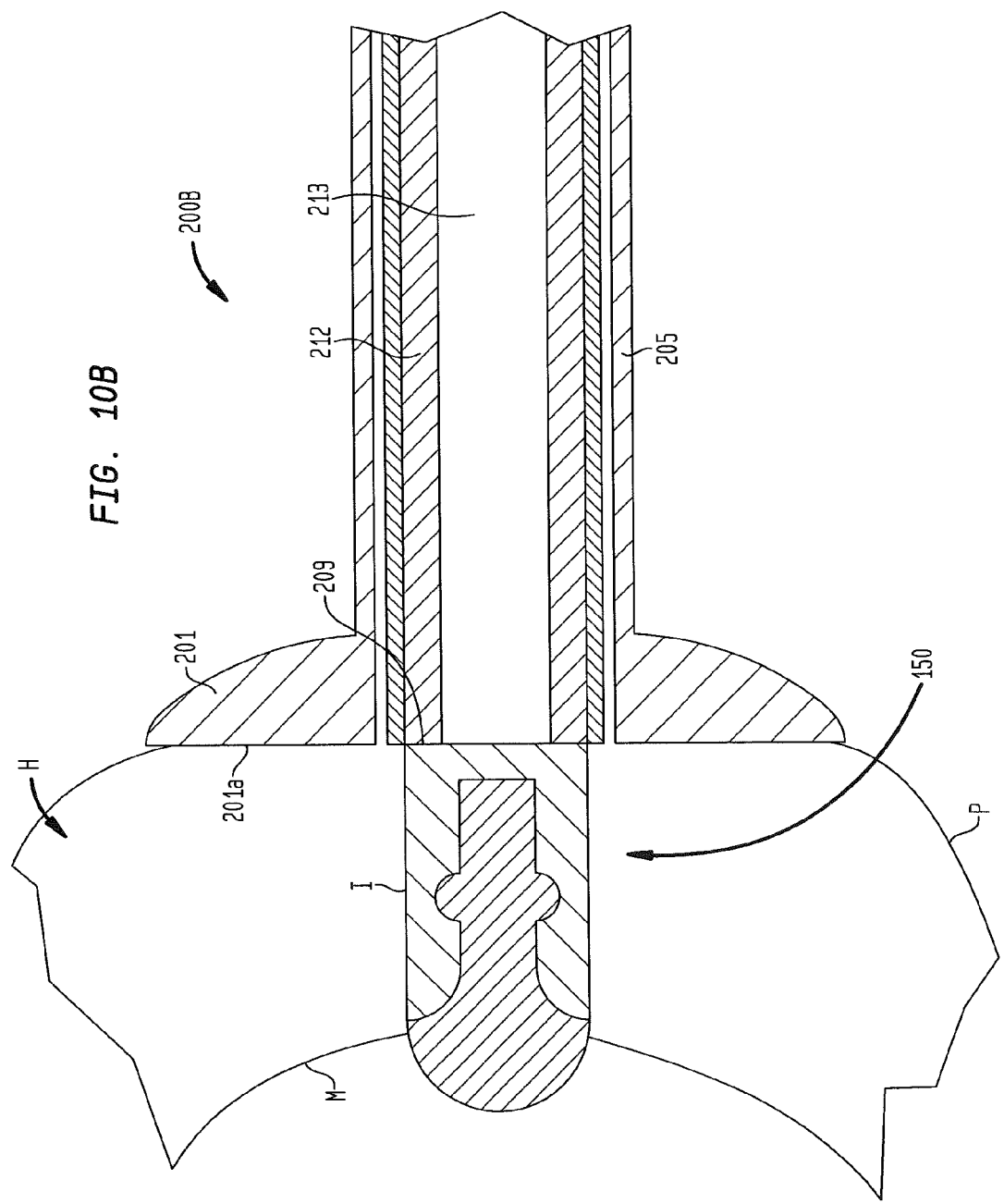

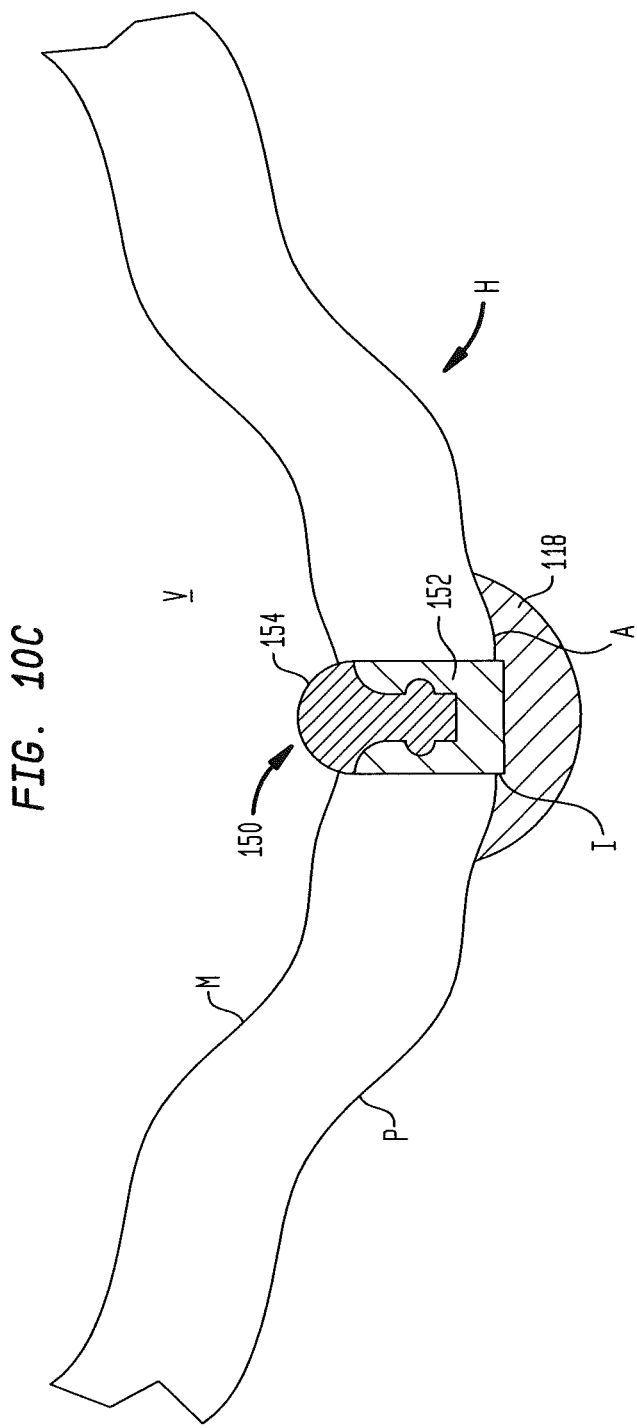

APEX CLOSURE DEVICE

CROSS REFERENCE TO RELATED APPLICATIONS

The present application is a continuation-in-part of U.S. patent application Ser. No. 13/146,789, filed Jul. 28, 2011, which is a national stage entry under 35 U.S.C. §371 of International Application No. PCT/US2010/000249, filed Jan. 29, 2010, which claims the benefit of the filing date of U.S. Provisional Patent Application No. 61/206,441, filed on Jan. 30, 2009, the contents of all of which are hereby incorporated herein in their entireties.

BACKGROUND OF THE INVENTION

The present disclosure generally relates to systems, devices, and methods for performing a cardiovascular surgical procedure, and more particularly for closing a puncture wound in a human or mammalian heart.

During a cardiac valve repair or replacement procedure, access to the interior of the heart may be necessary. To access the interior of the heart, physicians often conduct a median sternotomy. In a median sternotomy, the physician makes an incision along the center of the chest to divide the patient's sternum, thereby creating an access to the heart. Sternotomies result in long recovery times and involve a high risk of complications (e.g., infections) due to the lengthy surgery required for these unstable patients.

Rather than performing the more invasive median sternotomy, a less invasive thoracotomy introducer device may be used to access the interior of the heart and to provide a conduit through which other devices may be passed during the procedure. Such a miniaturized introducer aids the physician in inserting necessary repair or replacement materials into the heart while also limiting the level of physical invasiveness and the amount of blood loss. Some less invasive introducers have been developed over the years.

Although minimally invasive surgical procedures have several advantages, including less surgical trauma as compared with more invasive procedures, they still present challenges. Complications from vascular access may arise in patients who suffer from a variety of health issues including peripheral vascular disease. Some of these complications may be dealt with by more quickly and adequately sealing the conduit that was formed to provide access to the heart during the procedure.

Various devices and methods for sealing puncture wounds have been developed including those shown and described in commonly assigned U.S. Pat. No. 7,008,439, the entire contents of which are hereby incorporated herein by reference. However, a continuing need exists for devices and methods for closing access openings formed during minimally invasive surgical procedures, including devices and methods for the closure of openings formed in the apex of a patient's heart.

BRIEF SUMMARY OF THE INVENTION

The present disclosure generally relates to wound closure devices, systems, and methods, and in particular devices, systems, and methods for closing puncture wound within a human or mammalian heart.

The wound closure devices disclosed herein may be configured for placement within an opening, e.g., incision or puncture wound, accessing the interior of an organ. In an embodiment, a wound closure device may include a first section, e.g., an elongated shaft, and a second section, e.g., a cap, positioned at a distal end of the first section. The first and second sections may be positionable within the opening with the second section being proximate to the interior of the organ and separating the first section from the interior of the organ. The second section may include a flanged proximal end.

The first section may be formed from a material that is configured to promote tissue growth. In an embodiment, the first material may be a collagen-based material, a gelatin (e.g., porcine gelatin), or a polymer, e.g., a fibrous, resorbable, and/or non-thrombongenic polymer. The second material may be a polymer, e.g., a biodegradable polymer including but not limited to a polyglycolide (PGA) or polylacticcoglycolic (PLGA) polymer.

In an embodiment, a wound closure system may include an elongated shaft having a first longitudinally extending lumen, and a tube mounted in the first longitudinally extending lumen for sliding movement of the tube relative to the elongated shaft. A stop member may be positioned within the tube at a spaced distance from a distal end of the tube to define a loading zone in the tube between the distal end and the stop member. The tube may be slidable relative to the stop member, and a wound closure device may be positionable within the loading zone such that retraction of the tube relative to the stop member may cause deployment of the wound closure device from the loading zone. A lumen may extend through the shaft, and may be configured and adapted to eject a substance, such as a bioadhesive including but not limited to a glutaraledehyde-BSA adhesive.

In another embodiment, a wound closure system may include an anchor positionable on the interior of the organ, a self-expandable stent frame configured and adapted to be placed within the wound, a wound closure device, and a length of suture operatively coupling the anchor to the wound closure device. The anchor may be fixed relative to the interior of the organ to secure the wound closure device within the wound.

In yet another embodiment, a wound closure system may include a wound closure device, a holder having a distal end and a cavity extending inward from the distal end, the cavity being configured to receive the wound closure device therein, and a shaft supporting the holder, the holder being slidable relative to the shaft, wherein movement of the holder relative to the shaft causes deployment of the wound closure device from the holder.

In a further embodiment, a method for closing a wound in an organ may include providing a closure device having a leading end a trailing end, inserting the leading end of the closure device into the wound, advancing the closure device further into the wound so that the closure device is substantially positioned within the wound with the trailing end exposed to an exterior of the wound, and spreading a bioadhesive layer over the trailing end of the closure device. The method may also include placing a self-expandable stent into the wound, expanding the stent within the wound, fixing an anchor relative to one of the interior wall or the exterior wall of the organ, and inserting the closure device at least partially into the stent.

These and other features of the present disclosure will be more fully described with reference to the accompanying figures.

BRIEF DESCRIPTION OF THE DRAWINGS

By way of description only, embodiments of the present disclosure will be described herein with reference to the accompanying drawings, in which:

FIG. 3 is an isometric front view of the transapical mini-introducer of FIG. 1;

FIG. 4 is an isometric exploded view of the transapical introducer of FIG. 1;

FIG. 5 is a side view of a transapical introducer according to another embodiment of the present disclosure;

FIG. 6 is an isometric view of the transapical introducer of FIG. 5;

FIG. 9 is a side view of a wound closure device delivery apparatus;

FIG. 10B is a longitudinal cross-section of the distal end of the wound closure device delivery apparatus of FIG. 10A in a second condition relative to a heart;

FIG. 10C is a longitudinal cross-section of the distal end of the wound closure device delivery apparatus of FIG. 8 shown relative to the puncture wound in the heart;

DETAILED DESCRIPTION

Figure 1:
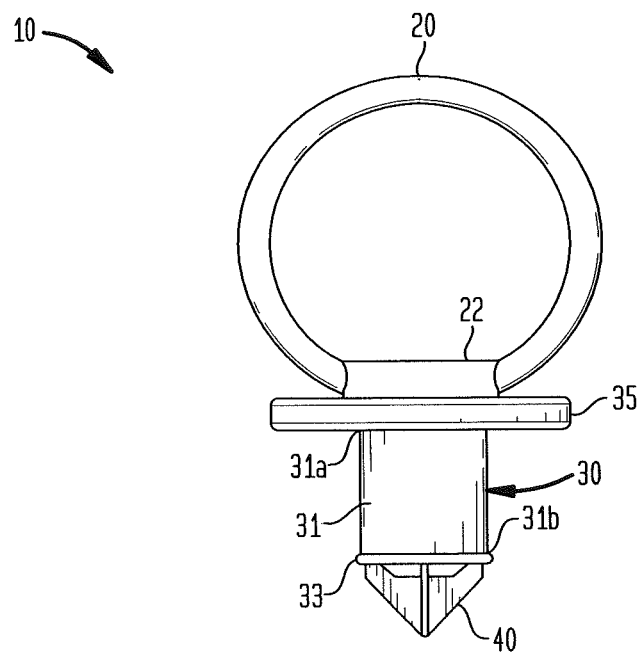
FIG. 1 is a side view of a transapical mini-introducer according to an embodiment of the present disclosure.

Particular embodiments of the present disclosure will be described with reference to the accompanying drawings. In the figures and in the description that follow, in which like reference numerals identify similar or identical elements, the term "proximal" will refer to the end of the device that is closer to the operator or user during use, while the term "distal" will refer to the end of the device that is farther from the operator or user during use.

FIGS. 1-4 show a transapical mini-introducer 10 according to an embodiment of the present disclosure. Mini-introducer 10 includes a feature for puncturing tissue (e.g., myocardium) and another feature for providing access to the interior of the heart. These features are coupled together. Consequently, a separate introducer sheath and a delivery device are not needed. The use of mini-introducer 10 minimizes bleeding and drops in blood pressure experienced when switching between puncture and introduction of a delivery device or an introducer sheath.

Mini-introducer 10 generally includes a ring 20, a hemostasis valve 30, and a punch or piercing element 40 configured to pierce cardiac tissue such as the myocardium. In some embodiments, punch 40 and hemostasis valve 30 can be integrated into a standard introducer. Punch 40 is coupled to ring 20. Ring 20 is releasably connected to hemostasis valve 30. Consequently, punch 40 and ring 20 can be separated from hemostasis valve 30. Mini-introducer 10 may be made of any suitable material capable of withstanding the force imposed when punch 40 punctures the myocardium at the apex of the heart, and when ring 20 is pulled or grasped to separate punch 40 from hemostasis valve 30.

With reference to FIGS. 3 and 4, ring 20 includes a base 22 and may be wholly or partly made of a material capable of withstanding the force imposed when a user (e.g., physician) or another instrument pulls, twists, or otherwise manipulates ring 20 to remove punch 40 from the myocardium. The diameter of ring 20 may vary depending on whether ring 20 is intended to be grasped by the user or by a grasping instrument. Ring 20 is connected to punch 40 through shaft 45. Shaft 45 includes a first end 45a attached to base 22 of ring 20 and a second end 45b connected to punch 40.

In some embodiments, punch 40 includes four blades 42 oriented substantially orthogonal to one another. Punch 40, however, may have more or fewer blades with any other shape or configuration suitable for puncturing the myocardium at the apex of the heart. In other embodiments, punch 40 may have a tapered or pointed shape. Irrespective of its shape, punch 40 is made wholly or partially of any material capable of puncturing the myocardium at the apex of the heart to access the interior of the heart without causing undue tissue damage.

Hemostasis valve 30 includes a tube or hollow member 31, which defines a bore or cavity therethrough (not shown). Hollow member 31 has a first end 31a and a second end 31b. First end 31a of hollow member 31 includes a shoulder 35 for abutting the apex of the heart, whereas second end 31b of hollow member 31 includes an annular rib 33 for assisting in securing hemostasis valve 30 to the heart. Hemostasis valve 30 may (additionally or alternatively) include multiple ribs 33 spaced along its axial length.

Hemostasis valve 30 further includes flexible flaps 37 (or any other suitable seal) positioned within the bore of hollow member 31 and adjacent to first end 31a. Flaps 37 may be wholly or partly made of silicon or any other resilient material suitable for permitting the passage of devices through hemostasis valve 30 while also preventing, or at least minimizing, blood leakage from the heart and limiting any drop in blood pressure. In the embodiment depicted in FIG. 4, hemostasis valve 30 includes four flaps 37 defining a cross-shaped slit, but hemostasis valve 30 may include more or fewer flaps. Regardless of the shape or number of flaps 37, the flaps are adapted to move between a substantially closed position (FIG. 4) in the absence of an instrument inside hemostasis valve 30 and an open position in the presence of an instrument within the hemostasis valve. In the substantially closed position, flaps 37 prevent, or at least inhibit, blood from exiting the heart through hemostasis valve 30. In the open position, flaps 37 allow the passage of one or more instruments or devices through the bore of hollow member 31. Hemostasis valve 30 may incorporate a duckbill seal instead of or in addition to flaps 37.

Figure 2:
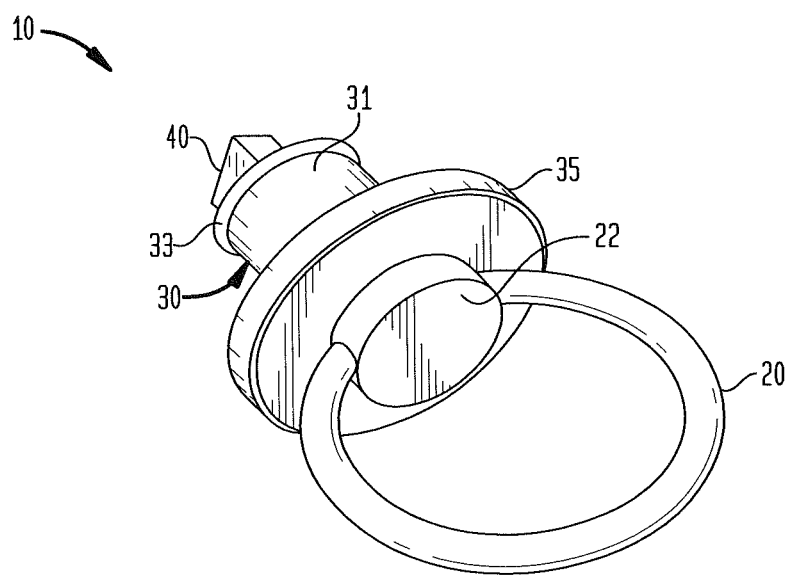
FIG. 2 is an isometric rear view of the transapical mini-introducer of FIG. 1.

The bore of hollow member 31 is dimensioned to receive shaft 45 and extends from the first end 31a to the second end 31b of the hollow member. To assemble mini-introducer 10, hemostasis valve 30 is positioned over punch 40 and shaft 45 until shoulder 35 abuts the base 22 of ring 20. At this point, the base 22 of ring 20 substantially or completely covers an opening leading to the bore of hollow member 31, as shown in FIG. 2. Once mini-introducer 10 has been assembled, shaft 45 is at least partially positioned inside hollow member 31 and punch 40 extends beyond the second end 31b of the hollow member. When shaft 45 is positioned inside hemostasis valve 30, hollow member 31 (completely or substantially) encloses shaft 45.

In some embodiments, mini-introducer 10 may include a detent release mechanism, such as a ball detent mechanism, to provide some resistance to the separation of ring 20 and punch 40 from hemostasis valve 30. The resistance produced by the detent release mechanism may be overcome by deliberate action to remove punch 40 from hemostasis valve 30.

In certain embodiments, the length of hemostasis valve 30 measured from first end 31a to second end 31b is about 0.5 inches. This length may ensure that the second end 31b of hemostasis valve 30 has accessed the interior of the heart without injuring the papillary muscles or the chordae. The length of the hemostasis valve 30 may be substantially similar to the length of shaft 45.

Figure 7:
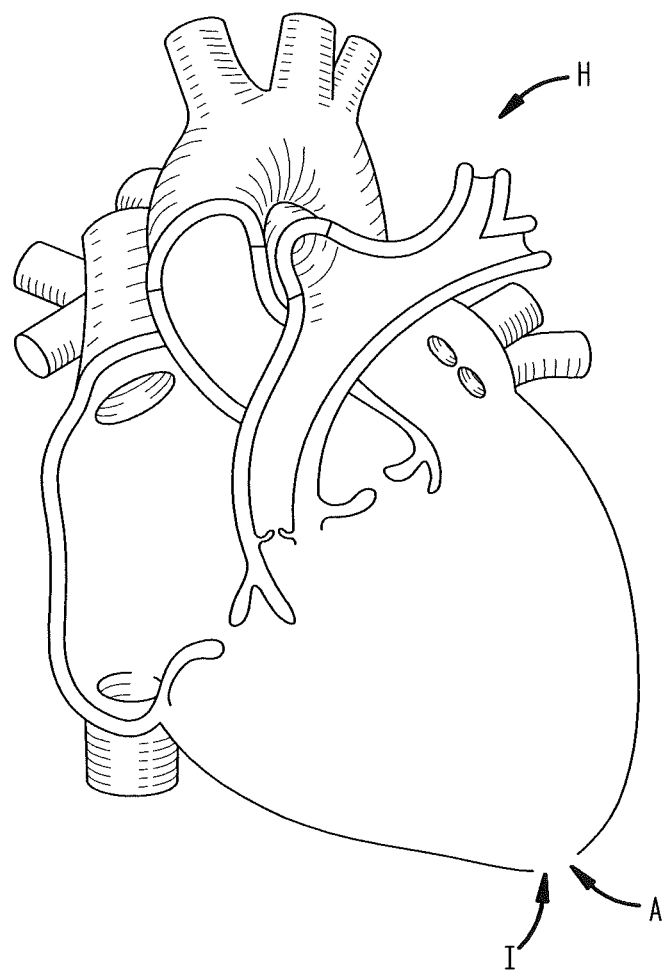
FIG. 7 is a side view of a patient's heart including a puncture wound at the apex thereof.

In any surgical procedure requiring access to the interior of the heart, a user (e.g., physician or other health care professional) may employ mini-introducer 10 to establish a conduit for the passage of other devices or instruments into the heart while minimizing blood loss and drops in blood pressure due to the puncturing of the apex A of the heart (FIG. 7). Mini-introducer 10 may be provided in a pre-assembled condition or may require assembly by the user. To assemble mini-introducer 10, the user slides hemostasis valve 30 over punch 40 and shaft 45 until shoulder 35 abuts the base 22 of ring 20. Once assembled, shaft 45 is at least partially positioned inside hollow member 31 and punch 40 extends beyond the second end 31b of the hollow member.

The user may gain access to the heart by performing a thoracotomy, spreading the incision, and moving the tissue or organs (e.g., the pericardium and the lungs) obstructing the user's view of the heart. The thoracotomy may be performed between the fifth and sixth intercostal spaces with, for example, a two to three inch incision. A purse string suture may be sewn at the apex of the heart using any suitable approach. Punch 40 may be aligned such that its tip is placed at the center of the purse string suture. Then, the user may grab ring 20 (directly or via a grasping implement or device) and advance mini-introducer 10 toward the patient's heart H to puncture the myocardium at the apex A with punch 40, thereby creating an access opening to the interior of the heart. The puncture is preferably created at the apex, where the myocardium is the thinnest. Mini-introducer 10 may be pushed toward the heart until shoulder 35 abuts the apex A. The purse string suture may then be cinched, or drawn, about mini-introducer 10.

While holding shoulder 35 against the apex A, the user may separate ring 20 and punch 40 from hemostasis valve 30 to leave the valve transapically positioned in the myocardium. To remove ring 20 and punch 40 from hemostasis valve 30, the user applies a pulling or twisting force to ring 20. This force may be applied directly by the user or through a grasping implement or instrument. In any case, ring 20 is pulled, twisted, or otherwise released from hemostasis valve 30 until ring 20 and punch 40 are removed from the patient, leaving hemostasis valve 30 behind in the myocardium. At this point, hemostasis valve 30 provides a conduit into the homeostatic environment (e.g., cardiopulmonary system) while also limiting both the amount of blood lost through the punctured myocardium and the drop in blood pressure that may occur as a result of accessing the interior of the heart. One or more instruments or devices, such as valvuloplasty balloons or collapsible prosthetic valve delivery systems, can be inserted into the patient's heart through the conduit created by hemostasis valve 30. When the user introduces an instrument through hemostasis valve 30, flaps 37 bend to permit passage of the instrument. Upon removal of the instrument, flaps 37 resiliently return to their original position, as shown in FIG. 4. In the original position, flaps 37 come together in the interior of hemostasis valve 30, thereby preventing, or at least inhibiting, blood from flowing out of the heart via hemostasis valve 30.

Another embodiment of the present invention may be configured so that the base 22 does not abut shoulder 35 in the assembled condition. A transapical introducer 60 in accordance with this embodiment is illustrated in FIGS. 5 and 6. Transapical introducer 60 is similar to, and may include some or all of the features of, transapical mini-introducer 10. Ring 70, hemostasis valve 80 and punch 90 may include some or all the features of ring 20, hemostasis valve 30, and punch 40, respectively. For example, hemostasis valve 80 includes a tube or hollow member 81 and a shoulder 85. Transapical introducer 60, however, includes an elongated shaft 75 instead of the shorter shaft 45 of transapical mini-introducer 10. Elongated shaft 75 connects ring 70 to punch 90. While shaft 45 of transapical mini-introducer 10 has a length that permits base 22 of ring 20 to abut shoulder 35 when punch 40 projects from the second end 31b of valve 30 (e.g., resulting in a distance of about 0.5 inches from base 22 to punch 40 in one embodiment), shaft 75 of transapical introducer 60 may have any length suitable to create a greater distance d (e.g., about six inches) between base 72 of ring 70 and punch 90. In some embodiments, hollow member 81 may extend beyond shoulder 85 toward ring 70. In those embodiments, a portion of hemostasis valve 80 may be positioned around elongated shaft 75 between shoulder 85 and ring 70.

The length of shaft 75 between shoulder 85 and punch 90 may be about the same as the length of shaft 45 (e.g., 0.5 inches), but shoulder 85 may be located at a greater distance (e.g., about 5.5 inches) from base 72 of ring 70 in comparison to the distance between shoulder 35 and base 22 of ring 20 of mini-introducer 10. A larger distance between base 72 and shoulder 85 permits ring 70 to reside outside of the patient's body rather than being introduced into and later extracted from the patient's body. The method of using transapical introducer 60 is substantially similar to the method of using transapical mini-introducer 10 described above.

As discussed above, each of transapical introducers 10, 60 includes a piercing element or punch 40, 90, respectively, which is configured and adapted to puncture the apex of the heart, thereby forming an incision to provide access to the interior of the heart. As shown in FIG. 7, heart H includes such an incision or puncture wound I at its apex A. Devices and methods for the closure and/or sealing of the puncture wound I are described herein with reference to FIGS. 8-13.

Figure 8:
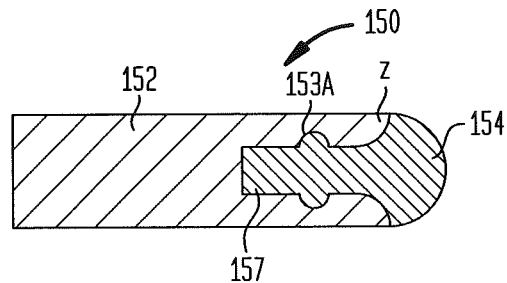
FIG. 8 is a cross-sectional view of one embodiment of a wound closure device.

One embodiment of a wound closure device 150 is shown in FIG. 8. Wound closure device 150 includes a shaft 152 and a cap 154 at a leading or distal end z of the shaft. The shaft 152 may be formed from a material that promotes tissue growth, e.g., a collagen-based tissue material. Alternatively or additionally, the shaft 152 may be formed from a polymer that is fibrous, resorbable, and non-thrombogenic. The cap 154 at the leading end z of the shaft 152 may inhibit blood in the heart H from contacting the material forming the shaft when the wound closure device 150 is placed within the puncture wound I. The cap 154 may be formed from any suitable material including a polymer, e.g., a biodegradable polymer such as a PGA or PLGA polymer. The cap 154 may have an arcuate or rounded shape at one end to facilitate insertion of the closure device 150 into the puncture wound I. The cap 154 may have a larger diameter than that of the shaft 152 or may be outwardly flared or flanged (not shown) to facilitate anchoring of the wound closure device 150 within the puncture wound I by inhibiting withdrawal of the wound closure device from the puncture wound after placement therein. The cap 154 may be secured to the shaft 152 frictionally or by a coupling means, e.g., suture.

As shown in FIG. 8, the cap 154 of wound closure device 150 is fit within a channel 157 defined within the shaft 152. The cap 154 may be formed from a resilient or semi-resilient material to facilitate a force-fit or frictional relationship between the cap and the channel 157, thereby inhibiting withdrawal of the cap from the channel. The channel 157 may include one or more retention features 153A that are configured and adapted to grasp or grip a portion of the cap 154 therein. As shown in FIG. 8, the retention feature 153A may be an annular groove formed in the channel 157 at a spaced distance from the distal end z of shaft 152. The material forming the cap 154 may be transitionable between a compressed condition and an expanded condition, and may be biased toward the expanded condition. In the compressed condition, the cap 154 may have a diameter that is smaller than that of the cap in the expanded condition. When the cap 154 is positioned within the channel 157, the cap expands to frictionally engage the channel 157 and/or to fill retention feature 153A.

Figure 8A:
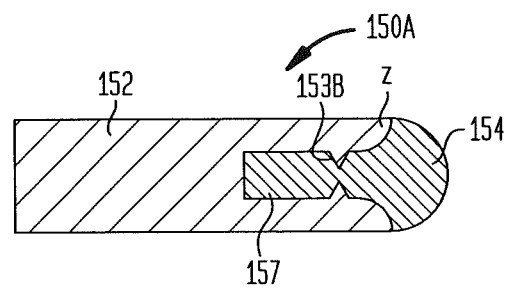
FIG. 8A is a cross-sectional view of another embodiment of a wound closure device.
Figure 8B:
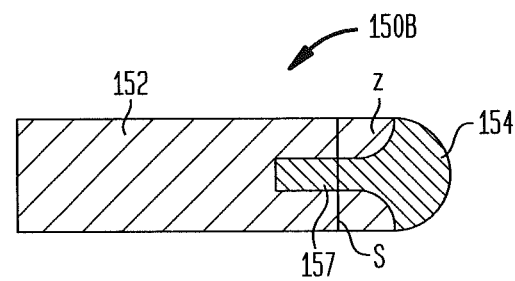
FIG. 8B is a cross-sectional view of yet another embodiment of a wound closure device.
Figure 8C:
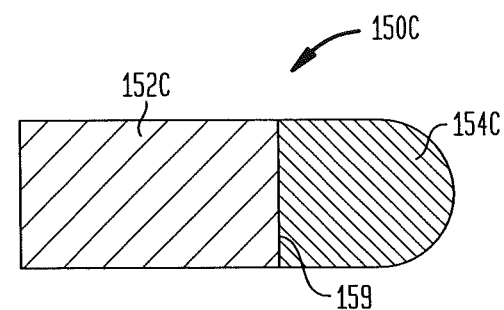
FIG. 8C is a cross-sectional view of a further embodiment of a wound closure device.

As shown in FIG. 8A, another embodiment of a wound closure device 150A includes all of the features of wound closure device 150 except that the one or more retention features 153B are tooth-like protrusions that are configured and adapted to frictionally engage the cap 154. As shown in FIG. 8B, a wound closure device 150B includes a length of suture S that passes transversely through both the shaft 152 and the cap 154 to secure the cap to the shaft, thereby inhibiting separation of the cap from within the channel 157 of the shaft. In another embodiment, as shown in FIG. 8C, a wound closure device 150C is substantially the same as the closure devices 150, 150A, and 150B, except that the shaft 152C may be secured to the cap 154C along a common plane 159 using an adhesive or other suitable securing means.

A wound closure device delivery apparatus 200A is shown in FIG. 9. The wound closure device delivery apparatus 200A may include a housing 203 supporting an elongated shaft 205, and a holder 220 operatively coupled to a distal end of the elongated shaft. The holder 220 is configured to releasably hold a wound closure device and to deploy the wound closure device into a puncture wound. The holder 220 may be operatively coupled to wound closure device 150, or to different wound closure devices, including wound closure devices 150A-150C. Once the apparatus 200A is moved to a desired position relative to a puncture wound, a rod (not shown) may be translated through a lumen extending longitudinally through the elongated shaft 205 to cause deployment of the closure device 150 from the holder 220. Actuators 202, 204 may be used to effect the advancement of the wound closure device to a predefined depth within the puncture wound I, and/or to eject a substance, e.g., a bioadhesive, after placement of the wound closure device within the puncture wound. After deployment of the wound closure device and/or ejection of a substance, the apparatus 200A may be removed from the surgical site.

Figure 10A:
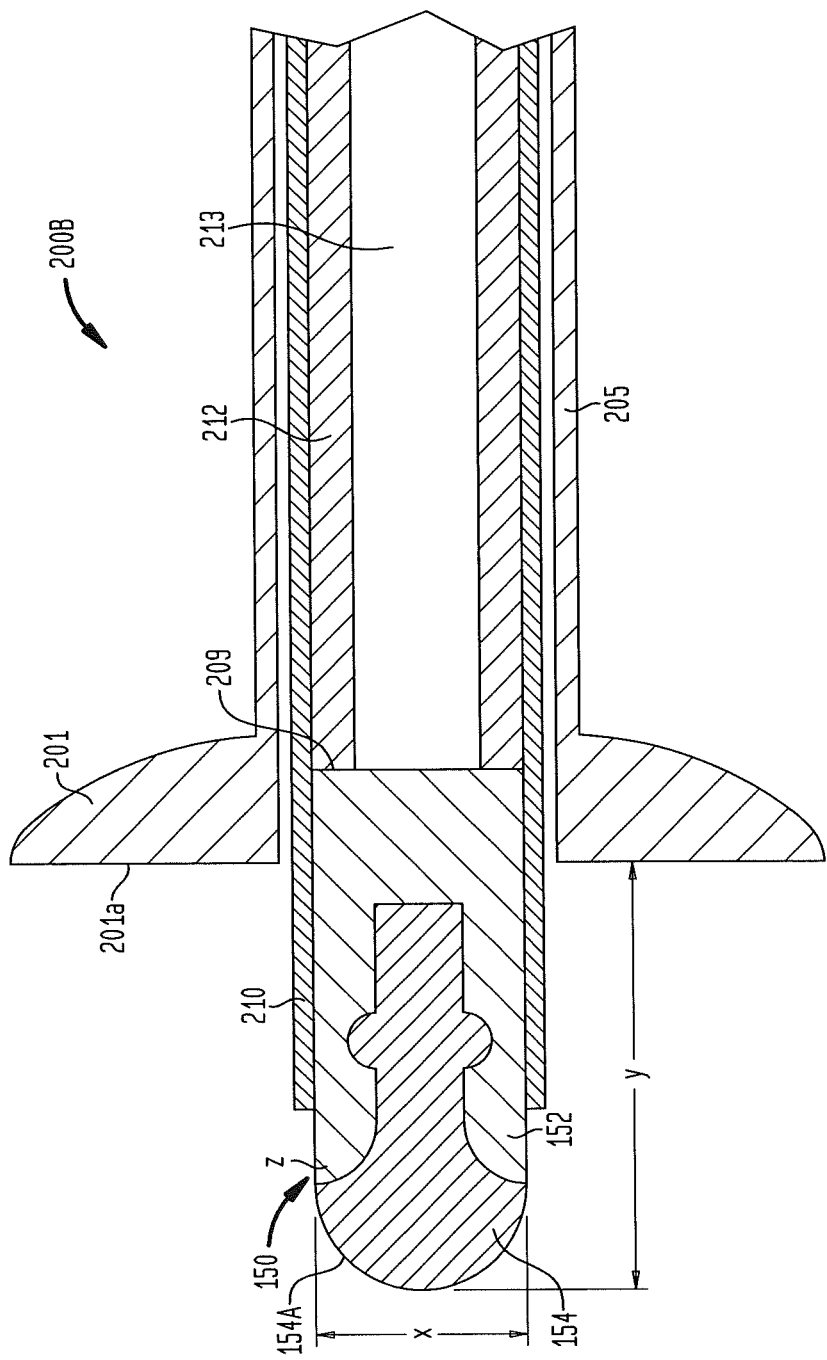
FIG. 10A is a longitudinal cross-section of the distal end of a wound closure device delivery apparatus in a first condition.
Figure 10D:
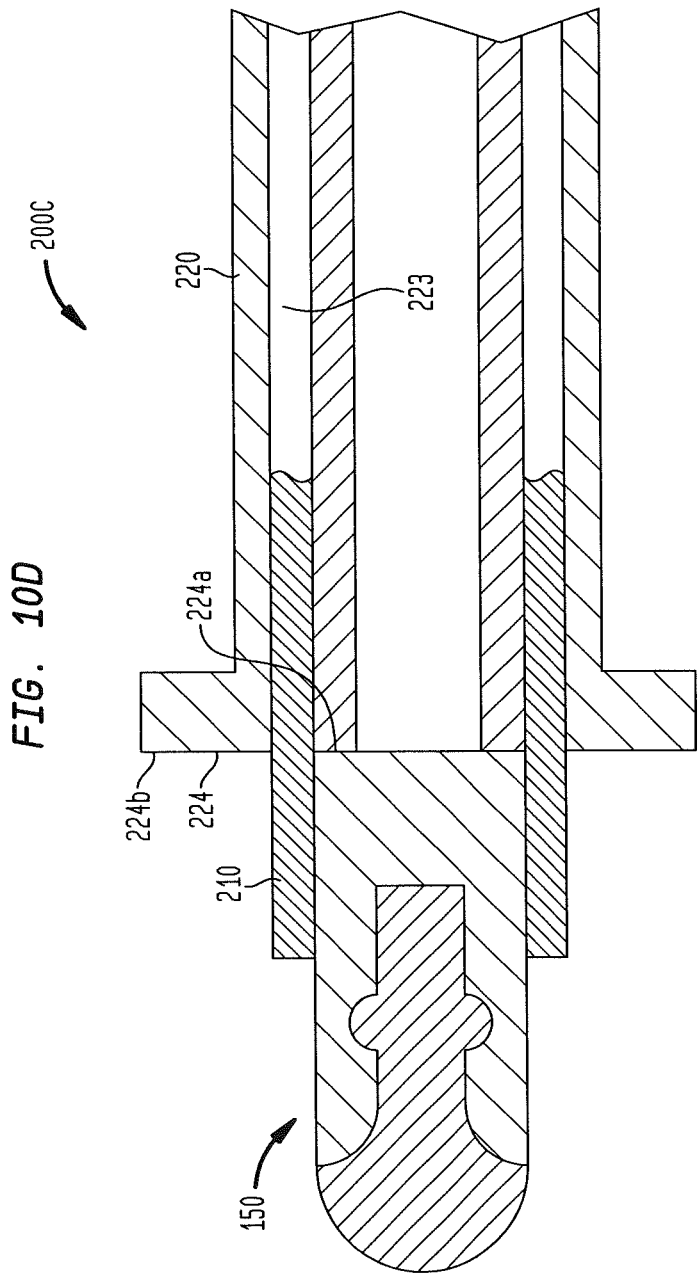
FIG. 10D is a longitudinal cross-section of the distal end of a wound closure device delivery apparatus in accordance with another embodiment of the present disclosure.

In a further embodiment, a wound closure device deployment apparatus 200B, shown in FIGS. 10A-10B, may include all of the features of apparatus 200A except where indicated otherwise. Apparatus 200B may include a housing, which supports elongated shaft 205, and a stop plate 201 at a distal end of the elongated shaft. The stop plate may have an annular or disc-shaped configuration. The elongated shaft 205 includes a lumen extending along a length of the shaft. A stop member 212 may be disposed within the shaft 205 and may be fixed in place relative to the stop plate 201. The stop member 212 may be tubular and may have a longitudinally extending lumen 213. A tube 210 may be disposed around the stop member 212 and may be translatable or slidable relative to the stop member. A wound closure device, such as wound closure device 150, may be loaded within tube 210. It is to be understood that tube 210 need not be cylindrical and may have a variety of other shapes.

The deployment of a wound closure device from the apparatus 200B is described with reference to FIGS. 10A-10B. Closure device 150 may be loaded within the tube 210 so that the closure device is frictionally engaged with the inner walls of the tube and is releasably secured within the tube. Closure device 150 may extend from a distal end of the stop plate 201 by a distance y, which may correspond to the depth by which the closure device may be initially inserted into puncture wound I. The tube 210 may be placed within the incision or puncture wound I within the heart H until the stop plate 201 contacts the outer wall of the heart. Tube 210 may be retracted through the longitudinally extending lumen of the elongated shaft 205, thereby drawing the closure device 150 against the distal end 209 of the stop member 212. Continued retraction of tube 210 causes the closure device 150 to protrude by increasing amounts from the tube until the closure device is deployed from the tube, as shown in FIG. 10B. When deployed, shaft 152 of wound closure device 150 may lie within the heart tissue and may not extend into the interior of the heart. Cap 154 may inhibit the interior of the heart from contacting shaft 152 of wound closure device 150.

Having been deployed from the tube 210, wound closure device 150 frictionally engages the walls lining puncture wound I, thereby inhibiting removal of the closure device once it is positioned within the puncture wound. The materials forming closure device 150 may promote tissue growth and may be bioresorbable. For example, wound closure device 150 may include a shaft 152 and a cap 154 at a leading or distal end z of the shaft, and shaft 152 may be formed from a material that promotes tissue growth. Thus, the wound closure device 150, when left within the puncture wound I, may facilitate healing thereof.

A substance, such as a bioadhesive, may be ejected through the lumen 213 of the stop member 212. As the bioadhesive is ejected onto the apex A of the heart H, it may form a bioadhesive patch 118 overlying the wound closure device 150 to help maintain the wound closure device within the puncture wound I, as illustrated in FIG. 10C. The bioadhesive may be spread over the surface of the pericardial tissue P of the heart H in a pre-defined manner to control the location of the bioadhesive prior to its setting and/or curing. The bioadhesive may be formed from a bioresorbable or a permanent material, and may form a bond with the heart tissue and/or the closure device 150. An example of a suitable material for the bioadhesive is a gluteraldehyde/BSA (bovine serum albumin) adhesive, which sets relatively quickly, forming a strong bond with tissue and reinforcing collagen. The bioadhesive may be terminally sterilized via gamma sterilization and may not require pre-mixing.

A wound closure device deployment apparatus 200C, which is similar to apparatus 200B described above, is shown in FIG. 10D. Rather than having an elongated outer shaft 205 and a separate tubular stop member 212 disposed in the shaft, apparatus 200C may include an elongated outer tube 220 and a stop member 224a formed integrally therewith at a distal end 224 thereof. An annular slot 223 formed between tube 220 and stop member 224a is sized to enable a tube 210 to translate therethrough. Tube 210 may project beyond the distal end 224 of tube 220, and is configured to support a proximal end of a wound closure device, such as device 150, at a fixed position relative to tube 220. The tube 220 may also include an integrally formed stop plate 224b projecting radially outward from the distal end 224 thereof for pressing against a tissue surface during deployment of the wound closure device.

Deployment of a wound closure device using apparatus 200C is substantially the same as described with respect to apparatus 200B except where indicated otherwise. A wound closure device, such as device 150, may be loaded within the portion of tube 210 that projects past the distal end 224 of tube 220 so that the wound closure device is frictionally engaged with the inner wall of tube 210 so as to be releasable therefrom. Tube 210 may then be placed within an incision or puncture wound of the heart until the stop plate 224b at the distal end 224 of tube 220 contacts the outer wall of the heart. Once positioned within the incision or puncture wound, tube 210 may be retracted into slot 223 of tube 220 while the stop member 224a prevents the wound closure device from retracting into tube 220. As a result, the wound closure device is ejected from tube 210 and is left in place within the incision or puncture wound. Thereafter, a substance, such as a bioadhesive, may be ejected through the interior of tube 220 to cover the wound closure device and/or the incision or puncture wound. Thereafter, a substance, such as a bioadhesive, may be ejected through the interior of tube 220 to cover the cover the wound closure device and/or the incision or puncture wound.

Figure 11:
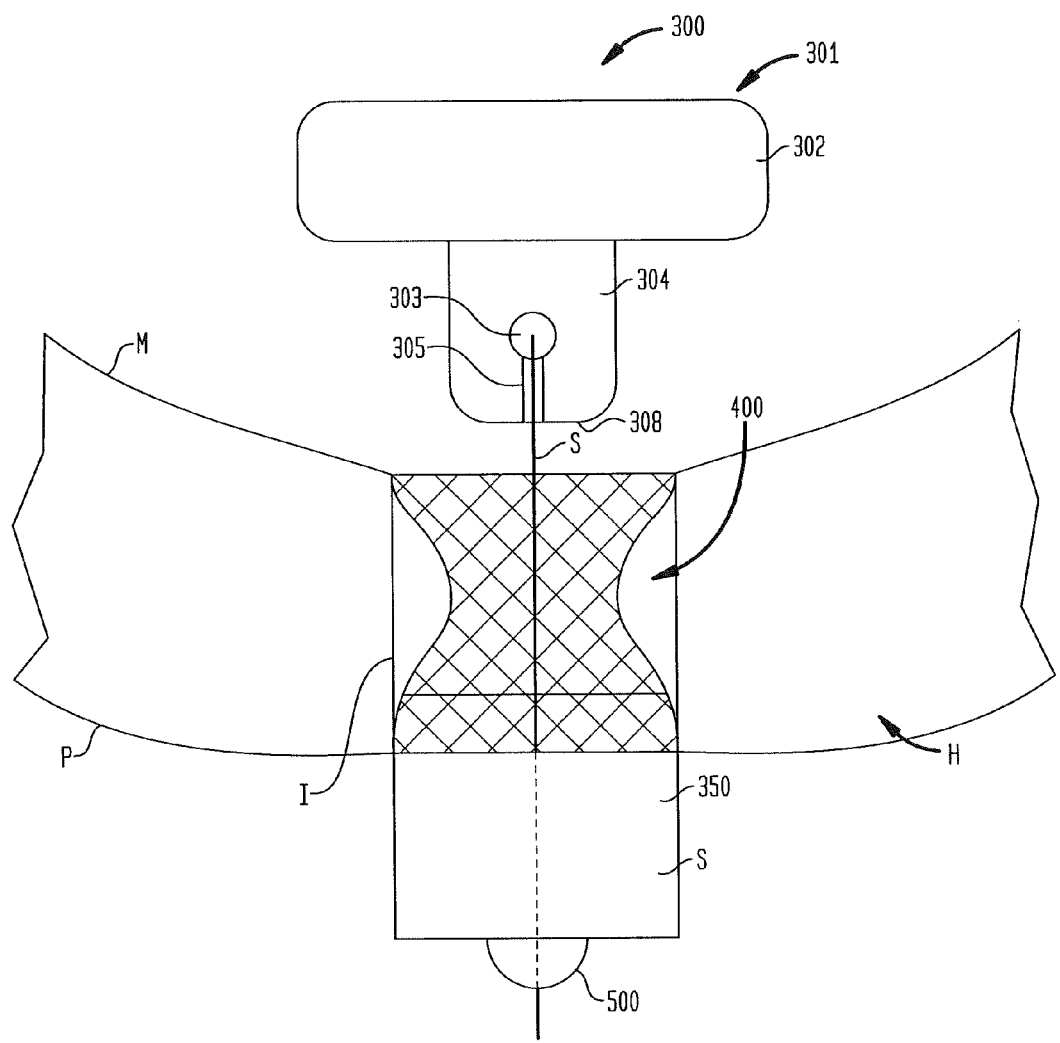
FIG. 11 is a side view of a wound closure system relative to the puncture wound in the heart.

In a further embodiment, shown in FIG. 11, a wound closure system 300 may include an anchor 301, a self-expandable stent frame 400, a plug 350, a retainer 500, and a length of suture S. The plug 350 may be formed from a material that promotes tissue growth, e.g., a collagen-based tissue material or a fibrous, resorbable, non-thrombogenic material. The anchor 301 may be formed from any suitable material including, but not limited to, materials having non-reactive properties that may be used within a patient's body, such as non-reactive polymers and metals.

The anchor 301 may include a base 302 that is dimensioned to interact with the inner wall M of the heart H, and a longitudinally extending shaft 304 that is configured and adapted to be placed within the tract of the puncture wound I. An aperture 303 may extend through the diameter of the shaft 304 to receive a length of suture S therethrough. A groove 305 may extend along the shaft 304 from the aperture 303 to the proximal end 308 of the shaft for receiving the suture S. The stent frame 400 is configured and adapted to be placed within the puncture wound I and to facilitate the placement of the plug 350 within the puncture wound by providing a suitable space for receiving both the plug 350 and the shaft 304 of the anchor 301. During use, the anchor 301 is placed on the inner wall M side of the heart H and the stent frame 400 is placed within the puncture wound I. Suture S may operatively couple the anchor 301 and the plug 350. In that regard, suture S may extend through aperture 303 of anchor 301, through plug 350, and through retainer 500. Retainer 500 may be a disk or button with one or more apertures therein for frictionally receiving the suture S so that the suture can be pulled in one direction through the retainer, but then will be held in place and will not travel back in the opposite direction through the retainer. The retainer 500 may also be a slip knot formed from the sutures. The suture S may be drawn through retainer 500 to draw the anchor 301 and plug 350 closer together. However, as retainer 500 prevents suture S from translating in the opposite direction, anchor 301 and plug 350 are inhibited from moving farther apart from one another. As the spacing between the anchor 301 and the plug 350 is reduced, the anchor is drawn toward the puncture wound I, and the plug is drawn into the wound and pushed into the stent frame 400. When the plug 350 is inserted substantially into the puncture wound I, the anchor 301 and the retainer 500 inhibit removal of the plug 350 from within the puncture wound. Any excess length of suture S may be cut or otherwise removed. A bioadhesive may be applied over the exposed end of the plug 350 and the surrounding tissue to strengthen the seal and/or closure of the puncture wound I. The materials of the closure system may be permanent and/or bioresorbable.

Figure 12A:
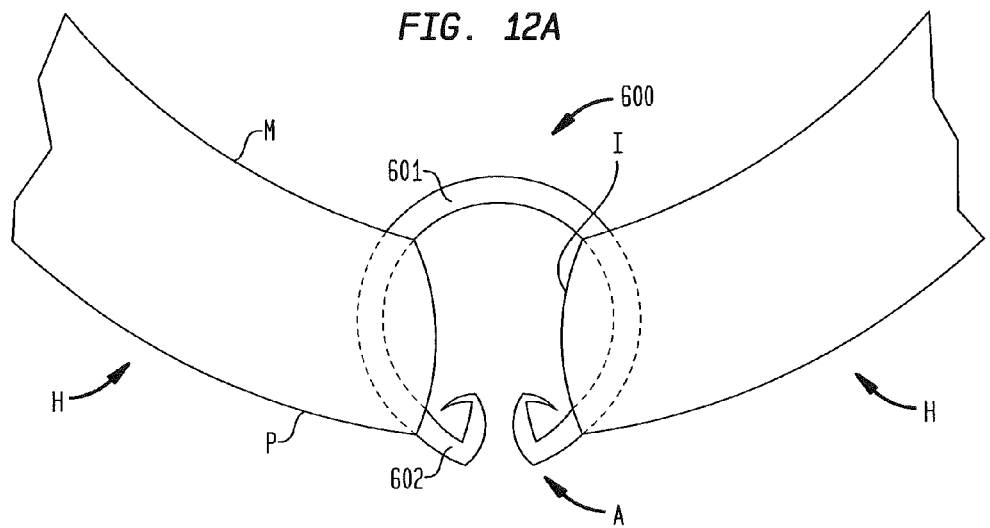
FIG. 12A is a side view of another embodiment of a wound closure device in a first state relative to the puncture wound in the heart.
Figure 12B:
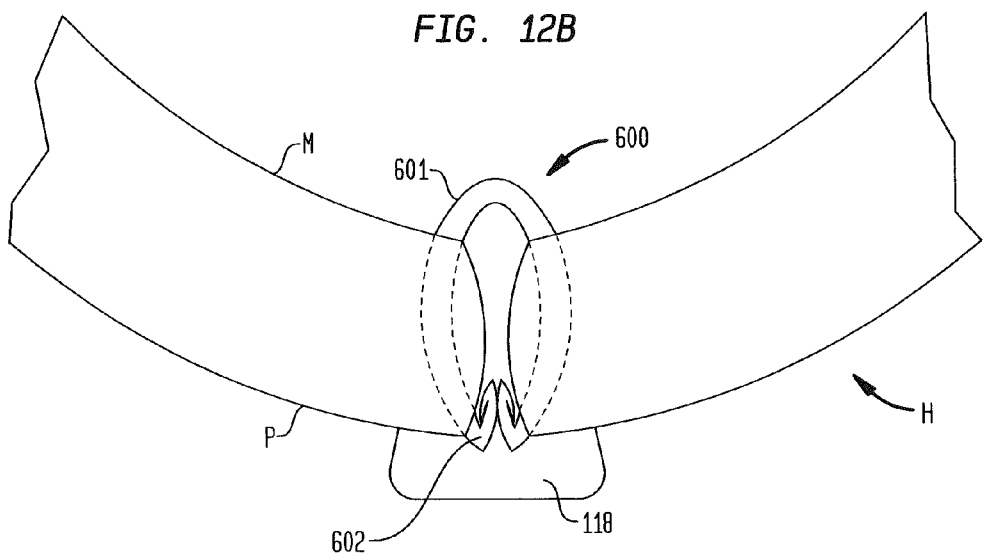
FIG. 12B is a side view of the wound closure device of FIG. 12A in a second state.

In another embodiment, a wound closure system 600 as shown in FIGS. 12A-12B may include a surgical staple or clip 601. The surgical staple or clip 601 may include one or more barbs 602 that facilitate insertion through the tissue of the heart H, as well as inhibit removal from the tissue once inserted. Optionally, the staple or clip 601 may be sutured to the tissue of the heart H after having been inserted therethrough. As shown in FIG. 12A, the staple or clip 601 joins the sides of the puncture wound I. As shown in FIG. 12B, the staple or clip 601 may be collapsed or compressed after having been secured through the sides of the puncture wound to draw the sides of the puncture wound together, thereby facilitating closure of the edges of the puncture wound. The staple or clip 601 may be formed from any suitable material including a bioresorbable material or a non-bioresorbable material, e.g., a titanium or nickel titanium alloy. As shown in FIG. 12B, a bioadhesive may be applied over the closed puncture wound I after placement of the staple or clip 601 to form patch 118, thereby reinforcing the closure and/or sealing of the puncture wound.

Figure 13:
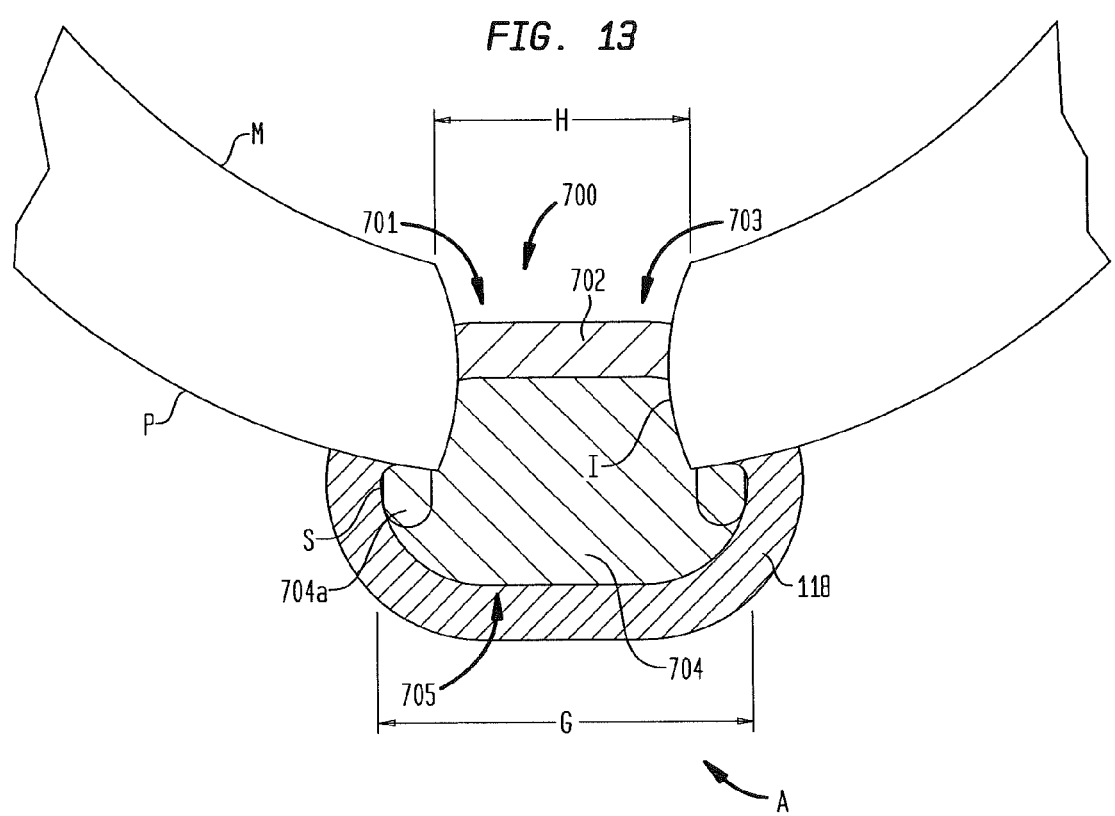
FIG. 13 is a cross-sectional view of another embodiment of a wound closure device relative to the puncture wound in the heart.

In still another embodiment shown in FIG. 13, a wound closure device 700 includes a plug 701 having a first section 704 and a second section 702 that are positioned adjacent to one another and that may be operatively coupled to one another by an adhesive, a suture, or any other attaching means. For example, the first section 704 and the second section 702 may have mating features (not shown) such as a protrusion and a groove so that one section may be press fit into the other. The first section 704 may have a flanged proximal end 704a so that insertion of the first section into the puncture wound I beyond a predetermined depth is inhibited. In particular, the first section 704 may have a first diameter H at its leading end 703 and a second diameter G at its trailing end 705, the second diameter being greater than the first diameter. The first section 704 may be formed from a material that promotes tissue growth, e.g., a collagen-based tissue material or a fibrous, resorbable, non-thrombogenic material. The second section 702 may be positioned adjacent the leading end 703 of the plug 701 and inhibits contact between the material forming the first section 704 and the blood in the heart H. The second section 702 may be formed from any suitable material including a polymer, e.g., a biodegradable or bioresorbable polymer such as a PGA or PLGA polymer.

During use, the plug 701 is inserted into the puncture wound I. The plug 701 may be resilient or semi-resilient to facilitate frictional engagement with the tissue surfaces lining the puncture wound I so as to form a sealing relationship. Suture S, e.g., a purse-string suture, may be used to secure the trailing end 705 of the plug 701 to the pericardial tissue P. A bioadhesive material may be applied over the trailing end 705 of the plug 701 to form a patch 118 to strengthen the closure and/or seal of the puncture wound I. Optionally, substances or materials may be applied that make the material forming the first section 704 more adhering to the tissue lining the puncture wound I.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, shafts 45 and 75 may have other lengths than those described and rings 20 and 70 may have other configurations. Also, for example, although the closure devices and methods have been described as being used for the closure and/or sealing of an incision at the apex of the heart, it is to be understood that the closure devices and methods described herein may be used in a variety of applications to effect closing and/or sealing of a wound.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A wound closure device for closing a wound opening accessing an interior of an organ, comprising:
    a first section formed from a first material configured to promote tissue growth, the first section extending in a longitudinal direction between a trailing end and a distal end, and including a defined channel extending proximally from the distal end, the channel having an open end with a first transverse cross-section at the distal end of the first section, a closed end with a second transverse cross-section at a spaced distance from the trailing end of the first section, and a transverse cross-section between the open end and the closed end that is larger than the first transverse cross-section and the second transverse cross-section so as to define a recess in the channel; and
    a second section positioned at the distal end of the first section, the second section having a protrusion positioned in the recess of the channel to secure the second section within the channel, the second section being formed from a second material different from the first material, wherein the first and second sections are sized for placement within the wound opening with the second section being proximate to the interior of the organ and separating the first section from the interior of the organ, the second section having a longitudinal axis and a distal end remote from the first section, the distal end of the second section being rounded in longitudinal cross-section.

2. The wound closure device according to claim 1, wherein the first material is a collagen-based material.

3. The wound closure device according to claim 1, wherein the first material is fibrous.

4. The wound closure device according to claim 1, wherein the first material is a gelatin.

5. The wound closure device according to claim 1, wherein the first material is resorbable.

6. The wound closure device according to claim 1, wherein the first material is non-thrombogenic.

7. The wound closure device according to claim 1, wherein the second material is a polymer.

8. The wound closure device according to claim 1, wherein the first section has a first diameter and the second section has a second diameter greater than the first diameter.

9. The wound closure device according to claim 1, wherein the second section has a compressed condition and an expanded condition and at least partially fills the recess in the channel upon movement from the compressed condition to the expanded condition.

10. A wound closure system for closing a wound through a wall of an organ to an interior of the organ, the wound closure system comprising:
    a self-expandable stent frame configured and adapted to be placed within the wound in the wall of the organ, the stent frame having an expanded condition;
    an anchor having a first end positionable in the interior of the organ and a second end receivable within the stent frame when the stent frame is in the expanded condition, the anchor being movable relative to the stent frame between an initial position in which the first end of the anchor is at a first position relative to the stent frame and a use position in which the first end of the anchor is at a second position relative to the stent frame, the second position being closer to the stent frame than the first position;
    a wound closure plug movable relative to the stent frame between a starting position in which the wound closure plug is spaced apart from the stent frame and an assembled position in which the wound closure plug is received within the stent frame when the stent frame is in the expanded condition; and
    a length of suture slidingly disposed through the wound closure plug and coupling the anchor to the wound closure plug.

11. The wound closure system according to claim 10, further comprising a retainer for holding the wound closure plug at a fixed distance from the anchor.

12. A method for closing a wound through a wall of an organ, the wall having an interior surface and an exterior surface, the wound accessing an interior of the organ, the method comprising:
    providing a closure device having a first section and a second section, the first section being formed from a first material configured to promote tissue growth, the first section including a distal end, a trailing end and a channel extending proximally from the distal end toward the trailing end, and the second section being a body positioned at the distal end of the first section and within the channel, the second section including a leading end at a spaced distance from the first section and being formed from a second material different from the first material, the leading end of the second section being rounded in longitudinal cross-section;
    placing a self-expanding stent into the wound in the wall of the organ;
    expanding the stent within the wound;
    fixing an anchor relative to one of the interior surface or the exterior surface of the wall of the organ;
    inserting the leading end of the closure device into the stent;

advancing the closure device into the stent so that the closure device is substantially positioned within the wall of the organ with the leading end exposed to the interior of the organ and the trailing end exposed to an exterior of the wound;

sliding a length of suture through the closure device to couple the closure device to the anchor at a fixed distance from the anchor; and applying a bioadhesive material over the trailing end of the closure device after the closure device has been advanced into the stent.

13. A wound closure device for closing a wound opening accessing an interior of an organ, comprising:

a first section formed a first material configured to promote tissue growth, the first section extending in a longitudinal direction between a trailing end and a distal end, and including a defined channel extending proximally from the distal end, the channel having an open end with a first transverse cross-section at the distal end of the first section, a closed end with a second transverse cross-section at a spaced distance from the trailing end of the first section, and a transverse cross-section between the open end and the closed end that is smaller than the first transverse cross-section and the second transverse cross-section so as to define a protrusion in the channel; and a second section positioned at the distal end of the first section, the second section having a recess, the protrusion in the channel residing in the recess in the second section to secure the second section within the channel, the second section being formed from a second material different from the first material, wherein the first and second sections are sized for placement within the wound opening with the second section being proximate to the interior of the organ and separating the first section from the interior of the organ, the second section having a longitudinal axis and a distal end remote from the first section, the distal end of the second section being rounded in longitudinal cross-section.

* * * * *